US008642341B2

(12) United States Patent
Kaplitt et al.

(10) Patent No.: US 8,642,341 B2
(45) Date of Patent: Feb. 4, 2014

(54) MATERIALS AND METHODS FOR GENE MEDIATED THERAPY OF PSYCHIATRIC DISORDERS

(75) Inventors: Michael Kaplitt, New York, NY (US); Brian L. Alexander, New York, NY (US)

(73) Assignee: Cornell University, Ithaca, NY (US)

( * ) Notice: Subject to any disclaimer, the term of this patent is extended or adjusted under 35 U.S.C. 154(b) by 474 days.

(21) Appl. No.: 12/740,725

(22) PCT Filed: Oct. 31, 2008

(86) PCT No.: PCT/US2008/082069
§ 371 (c)(1),
(2), (4) Date: Apr. 30, 2010

(87) PCT Pub. No.: WO2009/059192
PCT Pub. Date: May 7, 2009

(65) Prior Publication Data
US 2010/0263065 A1    Oct. 14, 2010

Related U.S. Application Data

(60) Provisional application No. 61/001,787, filed on Nov. 2, 2007, provisional application No. 61/001,894, filed on Nov. 5, 2007, provisional application No. 61/048,863, filed on Apr. 29, 2008.

(51) Int. Cl.
*C12N 15/63* (2006.01)
*C12N 15/86* (2006.01)
*C12N 15/00* (2006.01)

(52) U.S. Cl.
USPC ........ 435/455; 424/93.2; 424/93.6; 536/23.2; 536/24.1; 514/44

(58) Field of Classification Search
None
See application file for complete search history.

(56) References Cited

U.S. PATENT DOCUMENTS

| 4,797,368 | A |  | 1/1989 | Carter et al. |
| 5,139,941 | A |  | 8/1992 | Muzyczka et al. |
| 6,040,172 | A |  | 3/2000 | Kaplitt |
| 6,503,888 | B1 |  | 1/2003 | Kaplitt et al. |
| 2003/0152914 | A1 |  | 8/2003 | Kaplitt et al. |
| 2004/0248207 | A1 | * | 12/2004 | Okuse et al. ............ 435/7.2 |
| 2006/0129126 | A1 |  | 6/2006 | Kaplitt et al. |
| 2007/0231899 | A1 | * | 10/2007 | Waisman ............ 435/375 |
| 2010/0162422 | A1 | * | 6/2010 | Svenningsson et al. ...... 800/18 |

FOREIGN PATENT DOCUMENTS

WO    WO 2007/146372 A2    12/2007

OTHER PUBLICATIONS

Akechi et al, Diagnosis of psychiatric and psychologic disorders in patients with cancer, 2001, Japanese Journal of Clinical Oncology O31(5) pp. 188-294.*
Opalinska and Gewirtz, Nucleic-Acid Therapeutics: Basic Principles and Recent Applications, Nature Reviews, 2002, vol. 1, pp. 503-514.*
Russell, S. J., Replicating Vectors for Gene Therapy of Cancer: Risks, Limitations and Prospects, European J Cancer, 1994, vol. 30A (8), pp. 1165-1171.*

* cited by examiner

*Primary Examiner* — Maria Marvich
(74) *Attorney, Agent, or Firm* — Leydig, Voit & Mayer, Ltd.

(57) ABSTRACT

The invention provides materials and methods for p11-mediated therapy of psychiatric disorders. The invention provides vectors for increasing p11 expression and methods of treating a mammal with one or more symptoms of a psychiatric disorder. The invention also provides methods for improving a mammal's responsiveness to treatment for a psychiatric disorder. The invention further provides model animals for depression and depression therapy.

13 Claims, 4 Drawing Sheets

FIG. 1

```
atgccatctcaaatggaacacgccatgatgttacattcacaaattcgctggggataaaggctac
 M  P  S  Q  M  E  H  A  M  E  T  M  F  T  F  H  K  F  A  G  D  K  G  Y
ttaacaaggaggacctgagagtactcatggaaaaggagttccctgattttggaaaatcaaaagaccctg
 L  T  K  E  D  L  R  V  L  M  E  K  E  F  P  D  F  G  K  S  K  D  P  L
gctgtggacaaaataatgaaggaccgagtgtagacatgatgatttgtacacatgaagcagaaggaaagaag
 A  V  D  K  I  M  K  D  P  D  Q  F  Y  V  G  F  Q  S  F  S  L
attgcgggcctcaccattgcatgcaatgactatttgtagtacacatgaagcagaaggaaagaag [SEQ ID NO: 1]
 I  A  G  L  T  I  A  C  N  D  Y  F  V  H  M  K  Q  K  K [SEQ ID NO: 2]
```

FIG. 2

```
agaatacactcacaagccactccgcctctcgcctctcgcgcccgcgtccagctccgcctcgcgccagtccg
ccgcgcctcgcgccaaggcttcaacggaccacacaaatgccatctcaaatggaacacgccatgatg
                                       M  P  S  Q  M  E  H  A  M
gctgtggacaaaataatgaaggaccgagtgtagacatgatgatttgtagtacacatgaagcagaaggaaagaag
 A  V  D  K  I  M  K  D  P  D  Q  F  Y  V
gatggcaaagtgggcttccagagcttcttttccctaattgcgggcctcaccattgcatgcaatgactatttgta
 D  G  K  V  G  F  Q  S  F  S  L  I  A  G  L  T  I  A  C  N  D  Y  F  V
gtacacatgaagcagaaggaaagaagtaggcagaaatgagcagttcgctcctcgatagagttgtccaaag
 V  H  M  K  Q  K  K
ggtcgcttaaggaatctgccacgcttcccccatagaaggaaaagagaaacagagaaaaagagtaaatacagata
ttgtttgcatccccttgccctcaataaagttctttttagttcc [SEQ ID NO: 3]
```

MATERIALS AND METHODS FOR GENE MEDIATED THERAPY OF PSYCHIATRIC DISORDERS

CROSS-REFERENCE TO RELATED APPLICATIONS

This patent application is the U.S. national phase application of International Patent Application No. PCT/US2008/082069 filed Oct. 31, 2008, and claims the benefit of U.S. Provisional Patent Application No. 61/048,863, filed Apr. 29, 2008, U.S. Provisional Patent Application No. 61/001,894, filed Nov. 5, 2007, and U.S. Provisional Patent Application No. 61/001,787, filed Nov. 2, 2007, all of which are incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 5,495 Byte ASCII (Text) file named "Sequence Listing.TXT" created on Apr. 29, 2010.

BACKGROUND OF THE INVENTION

The pathophysiology of psychiatric disorders and, in particular, the cellular and molecular mechanisms responsible for the maintenance of severe forms of psychiatric disorders such as depression and other mood disorders remains poorly understood. This is so despite evidence indicating that common pathways are involved in multiple psychological disorders. For example, compounds that target or affect the serotonin and/or norepinephrine receptor systems have been used to treat a variety of psychiatric disorders including, for example, depression, affective disorders, psychoses, and addiction. Nonetheless, little progress has been made to identify genes and gene products that may be suitable for use in gene therapy of psychiatric disorders.

The p11 gene product, also known as s100A10, is a member of the s100 protein family that exists as a heterotetramer in which a central p11 dimer anchors two annexin A2 chains (Lewit-Bentley et al., *Cell. Biol. Int.*, 24: 799-802 (2000)). Northern blot analyses show that p11 expression, while ubiquitous, is low in liver, heart, and testes, moderate in brain, spleen, and thymus, and high in kidney, intestine, and lung (Saris et al., *J. Biol. Chem.*, 262: 10663-10671 (1987)). Although p11 shares significant sequence homology with other members of the S100 family, several amino acid substitutions and deletions render it unique (Gerke et al., *EMBO J.*, 4: 2917-2920 (1985); Glenney, *J. Biol. Chem.*, 261: 7247-7252 (1986)). Like other S100 family proteins, p11 possesses two EF-hand loops, although differences in amino acid sequence apparently compromise the ability of p11's EF loops to bind calcium, resulting in a permanently activated state (Rety et al., *Nat. Struct. Biol.*, 6: 89-95 (1999)). Cryo-electron microscopy studies show that the p11-annexinA2 heterotetramer fosters vesicle aggregation at the plasma membrane by forming symmetric junctions between opposing membrane surfaces (Lambert et al., *J. Mol. Biol.*, 272: 42-55 (1997)). In this way, the p11-annexinA2 complex may also stabilize membrane proteins in a particular configuration.

Studies have identified interactions between p11 and membrane-resident proteins of neuronal cells, including serotonin receptor. The relationship of p11 and trafficking protein for membrane-bound proteins was first identified in yeast two-hybrid studies. In particular, the tetrodotoxin-resistant sodium channel, Nav 1.8, and the potassium channel, TWIK-related acid-sensitive K (TASK) 1, were identified as binding partners for p11, and their translocation to the plasma membrane was reliant upon the presence of a p11-annexinII complex (Girard et al., *EMBO J.*, 21: 4439-4448 (2002); Okuse et al., *Nature*, 417: 653-656 (2002)). Further studies indicated that surface expression of these proteins were affected by levels of p11 (Poon et al., *FEBS Lett.*, 558: 114-118 (2004)). The trafficking of three other membrane-resident proteins also has been linked to p11 expression, namely the epithelial $Ca^{2+}$ channels TRPV5 and TRPV6, the acid-sensing ion channel ASIC1a, and the serotonin 1B receptor (Donier et al., *J. Biol. Chem.*, 280: 38666-38672 (2005); Svenningsson et al., *Science*, 311: 77-80 (2006); van de Graaf et al., *EMBO J.*, 22: 1478-1487 (2003)).

A recent report indicated that p11 overexpression increases surface expression of 5-HT1B, while p11 knockout mice demonstrate fewer binding sites for 5-HT1B receptor antagonists (Svenningsson et al., *Science*, 311: 77-80 (2006)). The report was not able to establish the role of p11 in depression-like states because of a number of confounding factors, some of which are associated with the study's use of transgenic mice. For example, the study could not distinguish between the developmental and physiological role of mice with a transgenically disrupted p11 gene. In another example, the study found that p11 overexpression in transgenic mice produced a generalized hyperactivity (Id. at 79).

Accordingly, there is a need for gene products that are useful in the treatment and understanding of psychiatric disorders, such as depression.

BRIEF SUMMARY OF THE INVENTION

The invention provides materials and methods useful in the treatment and understanding of psychiatric disorders. In one aspect, the invention provides a viral vector comprising a p11 nucleic acid. The viral vector can be, for example, a retrovirus vector, a lentivirus vector, an adenovirus vector, or an adeno-associated virus vector, and the p11 nucleic acid can be, for example, a p11 cDNA.

The viral vector of the invention can be used in a method of increasing p11 in a mammal. Generally, the method includes delivering a viral vector of the invention to the mammal, so as to cause expression of the p11 nucleic acid, thereby increasing p11 in the mammal. The method can include delivering the viral vector to a portion of the mammal's brain, e.g., the nucleus accumbens, thereby increasing the level of p11 in the portion of the brain of the mammal relative to the basal level of p11 in that portion of the brain.

The invention also provides a method of treating a psychiatric disorder in a mammal. The method generally includes delivering a therapeutic gene to the nucleus accumbens of a mammal suffering from a psychiatric disorder, thereby treating the psychiatric disorder. The therapeutic gene can be a p11 nucleic acid, which can be delivered in a viral vector of the invention to the nucleus accumbens.

The invention further provides a method for improving the responsiveness of a mammal to treatment for a psychiatric disorder. The method includes delivering a viral vector of the invention to the nucleus accumbens of a mammal suffering from a psychiatric disorder. The method further includes subjecting the mammal to a treatment for the psychiatric disorder, which is a treatment other than with gene therapy, whereby the mammal's responsiveness to treatment for the psychiatric disorder is improved.

Additionally, the invention provides a method of improving the responsiveness of a mammal to treatment for depression. The method includes delivering a viral vector of the invention to the nucleus accumbens of a mammal suffering from depression (e.g., major depressive disorder or refractory depression), and then subjecting the mammal to a treatment for depression other than with gene therapy, so as to improve the mammal's responsiveness to treatment for the psychiatric disorder.

Furthermore, the invention provides a method for treating one or more symptoms of depression in a mammal. The method includes delivering a therapeutic gene to the nucleus accumbens of a mammal exhibiting one or more symptoms of depression to thereby treat the one or more symptoms of depression. The method can be used to treat a mammal suffering from major depressive disorder or from refractory depression. The therapeutic gene can be a p11 nucleic acid, which can be delivered in a viral vector of the invention to the nucleus accumbens.

In another aspect, the invention provides an animal model for depression therapy, which can be produced by selectively delivering p11 nucleic acid to the nucleus accumbens of a non-human mammal.

In yet another aspect, the invention provides an animal model of depression produced by locally reducing a gene product, e.g., p11, in an isolated region of a brain, e.g., the nucleus accumbens, of a non-human mammal without reducing the gene product throughout the brain of the mammal.

BRIEF DESCRIPTION OF THE DRAWINGS

FIG. 1 depicts a p11 cDNA sequence, which has been designated SEQ ID NO: 1, and the p11 protein sequence, which has been designated SEQ ID NO: 2.

FIG. 2 depicts a p11 cDNA sequence (in bold) in the context of a flanking sequence from an adeno-associated virus (AAV) plasmid pAAV.siLuc.p11, which has been designated SEQ ID NO: 3. The underlined sequence within the p11 cDNA indicates a siRNA sequence, which has been designated SEQ ID NO: 4, and which can be used to knock down expression of p11.

DETAILED DESCRIPTION OF THE INVENTION

Figure 3:
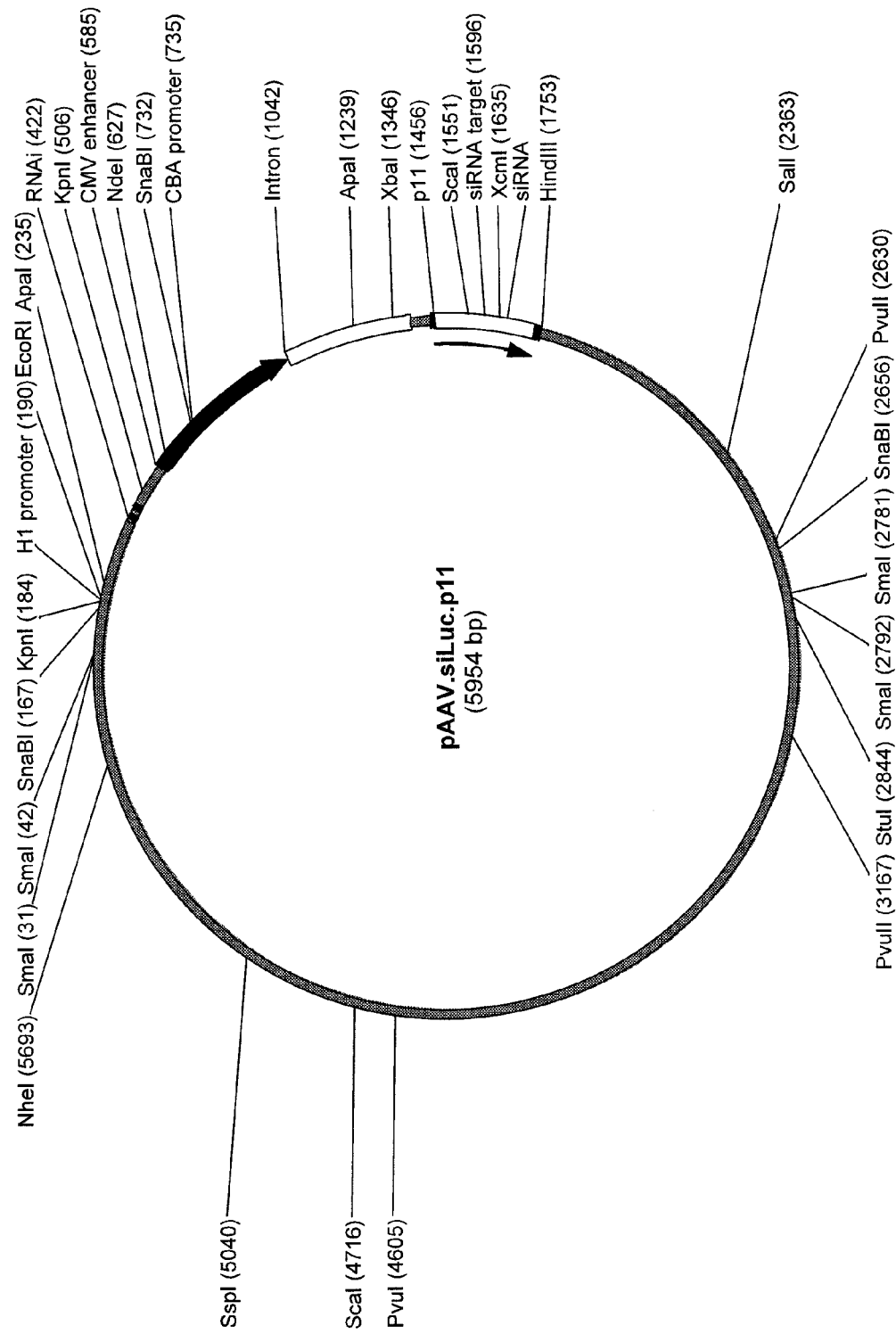
FIG. 3 is a plasmid map of the AAV plasmid that includes the p11 cDNA depicted in FIG. 2.

The invention provides materials and methods related to a gene transfer vector comprising a p11 nucleic acid. As used herein, the term "a p11 nucleic acid" refers to a nucleic acid that, when inserted into a gene transfer vector, can be subsequently delivered to a target cell and thereby increase the p11 gene product in the target cell. A p11 nucleic acid can include DNA, RNA, DNA or RNA nucleic acid analogs, or combinations thereof suitable for insertion into a gene transfer vector. A p11 nucleic acid can include a p11 coding strand, the complementing strand, or both, as appropriate to the gene transfer vector, e.g., a nucleic acid encoding p11. In certain gene transfer vectors, the p11 nucleic acid is preferably p11 cDNA, e.g., a cDNA encoding p11, such as SEQ ID NO: 1 or any other nucleic acid that encodes SEQ ID NO: 2.

As used herein the terms "mammal" and "mammalian" refer to any suitable mammal, including, but not limited to, a mouse, rat, cat, dog, guinea pig, hamster, rabbit, cat, dog, pig, cow, horse, primate, and human. The mammal typically is a human.

Mammalian genomic and coding sequences for p11 are known in the art and have been variously associated with the following alternative names. S100A10, 42C, p10, GP11, ANX2L, CAL1L, CLP11, Ca[1], ANX2LG, and MGC111133 (see, e.g., National Center for Biotechnology Information (NCBI) gene database entries for GeneID 6281 and RefSeq accession NM_002966, available through the NCBI web site; see also, e.g., Harder et al., *Gene*, 113(2): 269-274 (1992), which is specifically incorporated by reference herein in its entirety). The invention contemplates that a p11 nucleic acid can include one or more variations in the p11 coding sequence, so long as the one or more variations do not significantly alter the encoded p11 gene product function in one or more methods of the invention. Thus, for example, a p11 nucleic acid can include mutations that are silent or that do not significantly diminish the ability of the p11 gene product to complement endogenous p11 function in functional in vitro or in vivo assays.

The invention provides a viral vector comprising a p11 nucleic acid and regulatory sequences to drive expression of the p11 nucleic acid. Any suitable viral vector can be used in the inventive method, including, for example, parvoviral-based vectors (i.e., adeno-associated virus (AAV)-based vectors), lentiviral vectors, retroviral vectors, herpes simplex virus (HSV)-based vectors, AAV-adenoviral chimeric vectors, HIV virus-based vectors, and adenovirus-based vectors. Any of these gene transfer vectors can be prepared using standard recombinant DNA techniques described in, e.g., Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994).

Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. When employing pathogenic retroviruses, e.g., human immunodeficiency virus (HIV) or human T-cell lymphotrophic viruses (HTLV), care must be taken in altering the viral genomic to eliminate toxicity. A retroviral vector can additionally be manipulated to render the virus replication-incompetent. As such, retroviral vectors are thought to be particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells.

HSV-based viral vectors are suitable for use as a gene transfer vector to introduce nucleic acids into neurons. The mature HSV virion consists of an enveloped icosahedral capsid with a viral genome consisting of a linear double-stranded DNA molecule that is 152 kb. Most replication-deficient HSV vectors contain a deletion to remove one or more intermediate-early genes to prevent replication. Advantages of the herpes vector are its ability to enter a latent stage that can result in long-term DNA expression and its large viral DNA genome that can accommodate exogenous DNA up to 25 kb.

Adenovirus (Ad) is a 36 kb double-stranded DNA virus that efficiently transfers DNA in vivo to a variety of different target cell types. For use in the inventive methods, the virus is preferably made replication deficient by deleting select genes required for viral replication, such as, for example, all or portions of the E1, E2, and/or E4 regions. The expendable E3 region is also frequently deleted to allow additional room for a larger DNA insert. The vector can be produced in high titers and can efficiently transfer DNA to replicating and non-replicating cells. The newly transferred genetic information remains epi-chromosomal, thus eliminating the risks of random insertional mutagenesis and permanent alteration of the genotype of the target cell.

Adenoviral vectors can be derived from any serotype of adenovirus. Adenoviral stocks that can be employed as a source of adenovirus can be amplified from adenoviral serotypes 1 through 51, which are currently available from the American Type Culture Collection (ATCC, Manassas, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22-30, 32, 33, 36-39, and 42-47), subgroup E (serotype 4), subgroup F (serotypes 40 and 41), or any other adenoviral serotype. Preferably, however, an adenovirus is of serotype 2, 5, or 9.

AAV vectors are viral vectors of particular interest for use in gene therapy protocols (see, e.g., Santos Coura et al., *Virology Journal*, 4: 99 (2007)). AAV is a nonenveloped DNA virus, which is not known to cause human disease. AAV usually requires co-infection with a helper virus (i.e., an adenovirus or a herpes virus), or expression of helper genes, for efficient replication. In the absence of a helper virus, AAVs establish a latent infection within the target cell. The genome of AAV consists of an approximately 4.7 kb single-stranded linear DNA that contains two open reading frames (ORFs). The left ORF encodes nonstructural Rep proteins, and the right ORF encodes capsid (Cap) proteins VP1, VP2, and VP3. Each end of the AAV genome comprises a 145 base inverted terminal repeat (ITR), which contains the viral origin of DNA replication and the packaging signal. AAV ITR nucleotide sequences have been previously described, (see, e.g., Kotin et al., *Human Gene Therapy*, 5: 793-801 (1994); Berns "Parvoviridae and Their Replication" in Fundamental Virology, 2nd Edition (B. N. Fields and D. M. Knipe, eds.)).

AAV vectors used for administration of a therapeutic nucleic acid can have approximately 96%, or more of the parental genome deleted, such that only the ITRs remain. This eliminates immunologic or toxic side effects due to expression of viral genes. In addition, delivering the AAV Rep protein enables integration of the AAV vector comprising AAV ITRs into a specific region of genome, if desired. Host cells comprising an integrated AAV genome show no change in cell growth or morphology (see, for example, U.S. Pat. No. 4,797,368).

AAV vectors can be derived from any serotype of AAV, including, but not limited to, any of the 11 known AAV serotypes (i.e., AAV1, AAV2, AAV3, AAV4, AAV5, AAV6, AAV7, AAV8, AAV9, AAV10, and AAV11). AAV stocks that can be employed as a source of AAV can be amplified from AAV1, AAV2, AAV3, AAV4, or AAV5, which are currently available from the American Type Culture Collection (ATCC, Manassas, Va.), or from any other serotype of AAV available from any other source. Serotype 2 AAV (AAV2) has been the most extensively studied of all of the AAV serotypes. AAV2 can infect many different cell types, including skeletal muscle cells, neurons, vascular smooth muscle cells, and hepatocytes. In the context of the invention, an AAV2 gene transfer vector preferably is used to infect neurons.

The nonpathogenic and persistent long-term nature of AAV infection, combined with its wide range of infectivity, has made this virus an important candidate as a therapeutic gene transfer vector. However, if desired, the integrative properties of AAV can be conferred to adenovirus by constructing an AAV-Ad chimeric vector. For example, the AAV ITRs and nucleic acid encoding the Rep protein incorporated into an adenoviral vector enable the adenoviral vector to integrate into a mammalian cell genome.

Regulatory sequences for use in the vector of the invention can be provided from commonly used promoters derived from viruses such as polyoma, adenovirus 2, cytomegalovirus, and simian virus 40. The use of viral regulatory elements to direct expression of the protein can allow for high level constitutive expression of the protein in a variety of host cells. Ubiquitously expressing promoters also can be used, including, for example, the early cytomegalovirus promoter (see, e.g., Boshart et al., *Cell*, 41: 521-530 (1985)), herpesvirus thymidine kinase (HSV-TK) promoter (see, e.g., McKnight et al., *Cell*, 37: 253-262 (1984)), β-actin promoters (e.g., the human β-actin promoter as described by Ng et al., *Mol. Cell Biol.*, 5: 2720-2732 (1985)), and colony stimulating factor-1 (CSF-1) promoter (see, e.g., Ladner et al., *EMBO J.*, 6: 2693-2698 (1987)).

Alternatively, the regulatory sequences of the vector can direct expression of the gene preferentially in a particular cell type, i.e., tissue-specific regulatory elements can be used. Examples of tissue-specific promoters which can be used include central nervous system (CNS) specific promoters, such as neuron-specific promoters (e.g., the neurofilament promoter (Byrne et al., *Proc. Natl. Acad. Sci. USA*, 86: 5473-5477 (1989)) and glial specific promoters (see, e.g., Morii et al., *Biochem. Biophys. Res. Commun.*, 175: 185-191 (1991)). For example, the promoter can be tissue specific, such that it is (a) essentially inactive outside the central nervous system or (b) more active in the central nervous system than in other systems. For example, a promoter specific for the spinal cord, brainstem (medulla, pons, and/or midbrain), cerebellum, diencephalon (thalamus and/or hypothalamus), telencephalon (corpus stratium, cerebral cortex, and/or within the cortex, e.g., the occipital, temporal, parietal, and/or frontal lobes), or combinations, thereof. The promoter can be specific for particular cell types, such as neurons or glial cells in the CNS. If the promoter is active in glial cells, the promoter can be specific for astrocytes, oligodentrocytes, ependymal cells, Schwann cells, or microglia. If the promoter is active in neurons, the promoter can be specific for particular types of neurons, e.g., motor neurons, sensory neurons, or interneurons. Preferably, the promoter is specific for cells in particular regions of the brain, for example, the cortex, stratium, nigra, and/or hippocampus. In some preferred embodiments, the promoter is specific for the nucleus accumbens.

Suitable neuronal specific promoters include, but are not limited to, CMV/CBA, neuron specific enolase (NSE) (Olivia et al., *Genomics*, 10: 157-165 (1991); GenBank Accession No: X51956), and human neurofilament light chain promoter (NEFL) (Rogaev et al. *Hum. Mol. Genet.*, 1: 781 (1992); GenBank Accession No: L04147). Glial specific promoters include, but are not limited to, glial fibrillary acidic protein (GFAP) promoter (Morii et al., supra; GenBank Accession No. M65210), S100 promoter (Morii et al., supra; GenBank Accession No. M65210), myelin basic protein gene control region, which is active in oligodendrocyte cells in the brain (Readhead et al., *Cell*, 48: 703-712 (1987)), gonadotropic releasing hormone gene control region, which is active in the hypothalamus (Mason et al., *Science,* 234: 1372-1378 (1986), glutamine synthase promoter (Van den et al., *Biochem. Biophys. Acta.,* 2: 249-251 (1991); GenBank Accession No. X59834), and the preproenkephalin (PPE) upstream promoter region, as well as other promoters, described in U.S. Pat. No. 6,040,172. Suitable promoters for driving expression in the nucleus accumbens include those promoters associated with transcriptional markers for the nucleus accumbens (see, e.g., Chaldee et al., *Genome Res.,* 13: 1646-1653 (2003)).

In order to produce recombinant viral particles, a viral vector can be introduced into a suitable host cell using known techniques, such as by transfection. A number of transfection techniques are generally known in the art (see, e.g., Graham et al., *Virology,* 52: 456-467 (1973); Sambrook et al., supra; Davis et al., *Basic Methods in Molecular Biology,* Elsevier (1986); and Chu et al., *Gene,* 13: 97 (1981). Particularly suitable transfection methods include calcium phosphate co precipitation (see, e.g., Graham et al., supra), direct micro injection into cultured cells (see, e.g., Capecchi, *Cell,* 22: 479 488 (1980)), electroporation (see, e.g., Shigekawa et al., *BioTechniques,* 6: 742-751 (1988)), liposome mediated gene transfer (see, e.g., Mannino et al., *BioTechniques,* 6: 682-690 (1988)), lipid mediated transduction (see, e.g., Feigner et al., *Proc. Natl. Acad. Sci. USA,* 84: 7413-7417 (1987)), and nucleic acid delivery using high velocity microprojectiles (see, e.g., Klein et al., *Nature,* 327: 70-73 (1987)).

Suitable host cells for producing recombinant viral particles include, but are not limited to, microorganisms, yeast cells, insect cells, and mammalian cells, that can be, or have been, used as recipients of an exogenous nucleic acid molecule. Thus, a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen, or the fermentation system employed. Non-limiting examples include CHO dhfr-cells (see, e.g., Urlaub et al., *Proc. Natl. Acad. Sci. USA,* 77: 4216-4220 (1980)), 293 cells (see, e.g., Graham et al., *J. Gen. Virol.,* 36: 59 (1977)), and myeloma cells such as SP2 and NS0 (see, e.g., Galfre et al., *Meth. Enzymol.,* 73: 3-46 (1981)).

In one embodiment, the stable human embryonic kidney cell line 293 (e.g., ATCC Accession No. ATCC CRL1573) is used in the practice of the invention. The 293 cell line is readily transfected, and provides a particularly convenient platform in which to produce recombinant virions. For example, a human 293 cell line that has been transformed with adenovirus type 5 DNA fragments (Graham et al., supra) and expresses the adenoviral E1a and E1b genes (Aiello et al., *Virology,* 94: 460 (1979)) can be used to produce active adeno-associated viral particles.

Host cells comprising AAV vectors also must be capable of providing AAV helper functions in order to replicate and encapsidate the nucleic acid sequence flanked by the AAV ITRs to produce recombinant adeno-associated viral particles. AAV helper functions are generally AAV derived coding sequences which can be expressed to provide AAV gene products that, in turn, function in trans for productive AAV replication. AAV helper functions are used herein to complement necessary AAV functions that are missing from the AAV vectors. Thus, AAV helper functions include one or both of the major AAV open reading frames (ORFS), namely the Rep and Cap coding regions, or functional homologues thereof.

The AAV Rep coding region of the AAV genome encodes the replication proteins Rep 78, Rep 68, Rep 52, and Rep 40. These Rep proteins have been shown to possess many functions, including recognition, binding, and nicking of the AAV origin of DNA replication, DNA helicase activity, and modulation of transcription from AAV or other exogenous promoters. The Rep proteins are collectively required for replicating the AAV genome. The AAV Cap coding region of the AAV genome encodes the capsid proteins VP1, VP2, and VP3, or functional homologues thereof. AAV helper functions can be introduced into the host cell by transfecting the host cell with an AAV helper construct either prior to, or concurrently with, transfection of an AAV vector comprising a nucleic acid sequence. AAV helper constructs are thus used to provide at least transient expression of AAV Rep and/or Cap proteins to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products (see, e.g., Samulski et al., *J. Virol.,* 63: 3822-3828 (1989); and McCarty et al., *J. Virol.,* 65: 2936-2945 (1991)). A number of other vectors have been described which encode Rep and/or Cap proteins, for example, in U.S. Pat. No. 5,139,941.

As a consequence of the infection of the host cell with a helper virus, the AAV Rep and/or Cap proteins are produced. The Rep proteins also serve to duplicate the AAV genome. The expressed Cap proteins assemble into capsids, and the AAV genome is packaged into the capsids. This results in the AAV being packaged into recombinant adeno-associated viral particles comprising a nucleic acid sequence. Following recombinant AAV replication, recombinant AAV particles can be purified from the host cell using a variety of conventional purification methods, such as CsCl gradients or ion exchange chromatography. The resulting recombinant AAV particles are then ready for use for gene delivery to various cell types.

AAV vectors and methods for generating replication-defective virus vectors that are helper free are disclosed in U.S. Patent Application Publication 2003/0152914. AAV vectors and methods for AAV-mediated gene transfer to the brain and other parts of the central nervous nervous system are described in U.S. Pat. No. 6,503,888. Infusion devices and method for delivering viral vectors to the brain are described in U.S. Patent Application Publication 2006/0129126.

The invention provides a method for increasing p11 in a mammal by delivering a viral vector that includes a p11 nucleic acid to a mammal so as to cause expression of the p11 nucleic acid and, thereby, increase p11 in the mammal. In preferred embodiments, the method includes delivering the viral vector to at least a portion of the mammal's brain to thereby increase p11 relative to a basal level of p11 in the portion of the brain to which the p11 nucleic acid is delivered.

As used herein, the term "basal level of p11" generally refers to the level of p11 in at least a portion of the brain prior to delivery of the p11 nucleic acid. Basal p11 can refer to the average p11 level over a period of time, which can be as short or as long a period of time as is needed or practicable. Basal or increased levels of p11 can be determined directly by evaluating levels of p11 in the relevant portions of the brain. Alternatively, basal or increased levels of p11 expression can be determined indirectly by reference to a surrogate indicator of p11. Such surrogate indicators can include, for example, peripheral blood levels of p11, brain metabolic levels, and expression of one or more other p11-related gene products, which alone or collectively are indicative of p11 gene product expression. Improvement of one or more symptoms of a psychiatric disorder can also be a surrogate of increased p11 expression. The latter surrogate is particularly useful when the method of delivering a p11 nucleic acid to at least a portion of the mammal's brain to increase p11 relative to basal level of p11 is used in connection with the treatment of a mammal having one or more symptoms of a psychiatric disorder, as discussed more fully below.

The invention further provides a method of delivering a p11 nucleic acid to the nucleus accumbens of a mammal to thereby increase p11 in the nucleus accumbens relative to the basal p11 level in the nucleus accumbens. Preferably, the method includes selective or targeted delivery of the p11 nucleic acid to the nucleus accumbens, without significantly, or desirably at all, delivering the p11 nucleic acid throughout the brain. When the method includes selective or targeted delivery to the nucleus accumbens, the p11 nucleic acid can be delivered using a viral vector in accordance with the invention. Alternatively, when the method includes selective or targeted delivery of p11 nucleic acid to the nucleus accumbens, any other gene transfer methods known in the art can be used. Thus, for example, in connection with the selective delivery of a p11 nucleic acid to the nucleus accumbens, naked DNA, plasmid, and plasmid-liposome complexes can be used, instead of, or in addition to, the viral vectors disclosed herein.

The methods for delivering a p11 nucleic acid described herein can be used in the treatment of a mammal having one or more symptoms of a psychiatric disorder. For example, delivery of a p11 nucleic acid in accordance with the methods described herein can be used as gene therapy to treat a psychiatric disorder. In another example, the methods for delivering a p11 nucleic acid described herein also can be used to improve responsiveness to a treatment for a psychiatric disorder by delivering the p11 nucleic acid and subjecting the mammal to treatment for the psychiatric disorder other than with gene therapy, whereby the mammal's responsiveness to the non-gene therapy treatment is improved. In preferred embodiments of the foregoing methods, the mammal has proven refractory to other treatments for the psychiatric disorder. Psychiatric disorders and treatments therefor are discussed more fully below.

As used herein "psychiatric disorder" refers to one or more conditions described in the Diagnostic and Statistical Manual of Mental Disorders, Fourth Edition, published the American Psychiatric Publishing, Inc., Arlington, Va. (June 2000) ("DSM-IV"), which is specifically incorporated by reference herein in its entirety. Examples of psychiatric disorders include Axis I or Axis II disorders according to DSM-IV.

DSM-IV Axis I disorders can include conditions diagnosed in childhood or adulthood. For example, Axis I conditions include pervasive developmental disorder, autistic disorder, attention deficit-hyperactivity disorder, learning disability, conduct disorder, oppositional defiant disorder, and separation anxiety. Axis I conditions also can include (i) delirium, dementia, amnestic, and other cognitive disorders, (ii) substance abuse disorders (for example, dependence, abuse, intoxication, and withdrawal), (iii) schizophrenic disorders (for example, schizophrenia, schizophrenaform, and schizoaffective disorder), (v) mood disorders (for example, major depressive episode, major depressive disorder, dysthymic disorder bipolar I (manic), bipolar II (depression), cyclothymic disorder, anxiety, phobia, panic attack, obsessive/compulsive disorder, and post-traumatic stress disorder), and (vi) a somatiform disorder (for example somatization disorder, conversion disorder, pain disorder, hypochondriasis, and body dysmorphic disorder). Other Axis I conditions can include factitious disorder, eating disorder anorexia, bulimia, dissociative disorder, sexual disorder, sleep disorder, adjustment disorder, and premenstrual dysphoric disorder.

DSM-IV Axis II disorders can include conditions diagnosed in childhood or adulthood. Axis conditions can include (i) cluster A disorders associated with paranoid, schizophrenic, schizotypal, odd, or eccentric behavior, (ii) cluster B disorders associated with antisocial, borderline, histrionic, or narcissistic emotional/erratic behavior, and (iii) cluster C disorders associated with avoidant, dependent, obsessive/compulsive anxious or fearful behavior.

Additional psychiatric disorders include affective disorder, bipolar disorder, dysthymia, anxiety disorder, generalized anxiety disorder, panic disorder, obsessive compulsive disorder, post-traumatic stress disorder, and social phobia.

Moreover, the psychiatric disorder can be a mood disorder. The mood disorder can be any suitable mood disorder, such as depression, especially a major depressive disorder.

There are numerous art-known therapeutic regimes for the treatment of psychiatric disorders. Therapeutic regimes can include treatment with pharmacological compounds that modulate the brain's serotonin and/or norepinephrine systems. Such pharmacological compounds include, for example, tricyclic antidepressants, selective serotonin reuptake inhibitors (SSRI), selective norepinephrine reuptake inhibitors (SNRI), and serotonin antagonist and reuptake inhibitors (SARI). Specific exemplary pharmacological compounds include amitriptyline (ELAVIL™), clomipramine (ANAFRANIL™), desipramine (NORPRAMIN™), doxepin (SINEQUANT™), imipramine (TOFRANIL™), nortriptyline (PAMELORT™), protriptyline (VIVACTIL™), fluoxetine (PROZAC™), fluvoxamine (LUVOX™), paroxetine (PAXIL™), sertaline (ZOLOFT™), citalopram (CELEXA™), escitalopram oxalate (LEXAPRO™) duloxetine (CYMBALTA™) venlafaxine (EFFEXOR™), mirtazapine (REMERON™), nefazodone (SERZONE™), and desyrel (TRAZODONET™). The foregoing pharmacological compounds can be used singly or in any combination. The foregoing list of exemplary compounds is not exhaustive of those known in the art, which can be used in accordance with the invention.

Non-pharmacological therapeutic regimes include, for example, electroconvulsive therapy (ECT).

The foregoing methods for treating a mammal with one or more symptoms of a psychiatric disorder and for improving the responsiveness of a mammal to treatment for a psychiatric disorder can be especially useful when the mammal has proven refractory to previous treatment for the psychiatric disorder. In particular, the foregoing methods are especially useful to treat a mammal suffering from refractory depression, e.g., refractory major depressive disorder.

Additionally, the foregoing methods for treating a mammal with one or more symptoms of a psychiatric disorder and for improving the responsiveness of a mammal to treatment for a psychiatric disorder also can be especially useful to treat mammals having lower than standard levels of endogenous p11. A standard level of endogenous p11 refers to the level of endogenous p11 in one or more mammals that do not exhibit the same symptom(s) of a psychiatric disorder exhibited by the mammal to be treated. Preferably, the standard level of endogenous p11 is the average level of endogenous p11 in at least 5, 10, 25, 50, 100, 1,000, 5,000, or more mammals that do not exhibit the same symptom(s) of a psychiatric disorder exhibited by the mammal to be treated. Levels of p11 can be determined as for basal p11 levels, e.g., by directly evaluating levels of p11 in the relevant portions of the brain. Alternatively, p11 levels can be determined indirectly by reference to a surrogate indicator of p11. Such surrogate indicators can include, for example, peripheral blood levels of p11 gene product, brain metabolic activity, and expression of one or more other p11-related gene products, which alone or collectively are indicative of p11 gene product expression.

The foregoing methods for treating a mammal with one or more symptoms of a psychiatric disorder and for improving the responsiveness of a mammal to treatment for a psychiatric disorder also can be especially useful to treat mammals whose genome comprises one or more deleterious mutations in the p11 gene. As used herein the term "deleterious mutation" refers to a mutation that compromises the function of a gene product or reduces expression of the gene product in the mammal. Thus, a deleterious mutation can be a loss of function mutation, such as, for example, a mutation that truncates at least 10%, 15%, 20%, 25%, 30%, 40%, 50%, 60%, or more of the mammal's p11 gene product. Other loss function mutations include region mutations in one or more essential functional domains or essential conserved structures of the mammal's p11 gene product. Essential or conserved structures may include those involved in the formation of the p11-annexin A2 complex and/or the complex's ability to bind calcium and properly locate to the plasma membrane. Deleterious mutations also can include mutations in the transcriptional regulatory regions (e.g., the promoter or enhancer regions) upstream of the p11 coding sequence that reduce expression of the mammal's p11 gene product. For example, specific deletions in the promoter region of the p11 gene have been shown to adversely affect p11 expression (Huang et al., *Gene,* 310: 133-42 (2003)).

The foregoing methods for treating a mammal with one or more symptoms of a psychiatric disorder and for improving the responsiveness of a mammal to treatment for a psychiatric disorder can be useful to treat mammals whose genome comprises one or more deleterious mutations in the gene for a serotonin receptor. Serotonin receptor genes are known in the art and include HTR1A, HTR1B, HTR1D, HTR1E, HTR1F, HTR2A, HTR2B HTR2C, HTR3A, HTR3C, HTR3D, HTR3E, HTR4, HTR5A, HTR5B, HTR6, and HTR7.

It has been surprisingly discovered that the localized expression of p11 in a portion of the brain (specifically, the nucleus accumbens) does not result in the generalized hyperactivity previously associated with p11 overexpression (Svenningsson et al., supra, at 79). Accordingly, in preferred embodiments of the foregoing methods for treating a mammal with one or more symptom of a psychiatric disorder and for improving the responsiveness of a mammal to treatment for a psychiatric disorder, the methods avoid producing a general hyperactivity in the mammal to which the p11 nucleic acid is delivered.

The invention described herein further provides an animal model for depression having locally reduced expression of a gene product in an isolated region of the brain of an animal, such as the nucleus accumbens. Preferably, the animal is a non-human mammal. Also preferably, the reduced gene product is p11. The animal model can be made by locally reducing expression of a gene, e.g., a gene encoding p11, in an isolated region of a brain, e.g., the nucleus accumbens, of the animal. The localized reduction of gene expression can be accomplished using any method that avoids reducing the gene's expression throughout the mammal's brain. For example, localized reduction can be accomplished using a viral vector, plasmid, phage, transposon, cosmid, virus, or virion to selectively deliver a nucleic acid, e.g., anti-sense RNA or small interfering RNA, to the nucleus accumbens of the non-human mammal. Alternatively, a transgenic non-human mammal model for depression can be made using a system that selectively disrupts the p11 gene in the isolated region of the brain, e.g., the nucleus accumbens, without affecting p11 gene expression elsewhere in the brain. For example, a system for selectively disrupting the p11 gene can include generating mice having at least a portion of essential genomic p11 coding sequence or regulatory sequence flanked by sites (e.g., lox sites), which are recognized by a recombinase (e.g., the p1 phage Cre recombinase). The mice can be bred or genetically engineered to further include the coding sequence for Cre recombinase coding sequence operably linked to a regulatory sequence that (a) drives expression of the Cre recombinase in the nucleus accumbens (or in some other isolated region of the brain) and (b) does not drive expression of Cre recombinase throughout the entire brain. Exemplary regulatory sequences can include those regulatory sequences that drive expression of transcriptional markers for the nucleus accumbens (see, e.g., Chaldee et al., *Genome Res.,* 13: 1646-1653 (2003)). When expressed in the nucleus accumbens, the recombinase selectively excises the p11 genomic region flanked by the recombinase recognition sites in the nucleus accumbens.

The following examples further illustrate the invention but, of course, should not be construed as in any way limiting its scope.

EXAMPLE 1

This example demonstrates that reducing p11 in the nucleus accumbens is associated with a psychiatric disorder and provides a non-human mammalian model for depression.

Adeno-associated virus serotype 2 (AAV2) backbone, which has been previously described and shown to effectively carry out gene transfer in both rodent and human models (Kaplitt et al., *Lancet,* 369: 2097-2105 (2007); Musatov et al., *Proc. Natl. Acad. Sci. USA,* 104: 2501-2506 (2007), both of which are specifically incorporated by reference herein in their entirety), was engineered to express a small interfering RNA (see underlined sequence in FIG. 2). The resulting vector ("AAV-p11-siRNA") profoundly blocked p11 expression in vitro.

Two mouse groups (n=10) received bilateral nucleus accumbens injections of AAV-p11-siRNA or control vector. The mouse groups are referenced herein as the "knockdown group" or "control" respectively. Behavioral testing began 6 weeks later, when expression from AAV vectors usually peaks. Behavioral testing included mouse tail suspension test (TST), open filed test, and forced swim test (FST).

In TST, the p11 knockdown group displayed a significant increase in immobility compared to control group ($p<0.05$), consistent with a more depressive phenotype. A significant increase in knockdown group thigmotaxis (wall-hugging behavior) relative to control was also observed in open-field testing ($p<0.01$), indicating a heightened level of anxiety. The knockdown group also displayed a greater duration of immobility in the forced swim test (FST) ($p<0.01$), which is another standard model suggestive of a more depressed phenotype.

The foregoing results confirm that reduction of p11 expression correlates with one or more symptoms of a psychiatric disorder. The foregoing results also illustrate that selective reduction of p11 expression in the nucleus accumbens of a non-human mammal produces an animal model of depression in accordance with the invention. The results are surprising, inasmuch as the nucleus accumbens is almost exclusively known for its pivotal role in brain pathways regarding pleasure, reward, and addiction and is only infrequently implicated in depressive-like states.

EXAMPLE 2

This example demonstrates that reduction of p11 in the nucleus accumbens interferes with responsiveness to antidepressants.

Knockdown and control groups of mice were transfected with AAV-p11-siRNA or control AAV vector, as described in Example 1. An additional control group was not transfected with any virus. The mice were subsequently treated with the antidepressant imipramine. Mice injected with control vector or no virus displayed the expected dramatic effects of imipramine, which is decreased immobility on the TST and FST. The knockdown group injected with AAVp11-siRNA displayed a blunted response to antidepressant treatment.

The foregoing results indicate that localized reduction of p11 levels in the nucleus accumbens can interfere with the pharmacological effects of an antidepressant, thereby implicating nucleus accumbens p11 in the function of antidepressants.

EXAMPLE 3

This example illustrates a viral vector according to the invention. This example also demonstrates that localized delivery of a p11 nucleic acid to the nucleus accumbens does not induce general hyperactivity.

The AAV plasmid shown in FIGS. 2 and 3 was used to generate a virus vector, which expresses the p11 gene product and which has the same AAV2 backbone described in Example 1. The resulting virus vector ("AAV-p11," which is SEQ ID NO: 3) was injected into the nucleus accumbens of normal adult mice. Behavioral testing, including TST, open field test, and FST, was carried out in parallel with that described in Example 1, which showed that p11 knockdown in the nucleus accumbens results in increased immobility and thigmotaxis relative to control. Notably, mice transfected with AAV-p11 failed to behave in a manner that differed significantly from the control group (transfected with control vector) during TST, open field test, and FST.

These results differ from those previously reported for transgenic mice that overexpressed p11 and were generally hyperactive (Svenningson et al., supra, at 79). Accordingly the foregoing results indicate that a viral vector according to the invention, when transfected into the nucleus accumbens, does not result in a generalized hyperactive phenotype.

EXAMPLE 4

This example demonstrates that localized genetic transfer of a p11 nucleic acid to the nucleus accumbens can correct a depressive phenotypes without inducing general hyperactivity.

Three groups of p11 knockdown mice (as in Example 1) were transfected with no virus, control virus vector, and the AAV-p11 virus vector of Example 3, respectively. Each knockdown transfectant group was compared to a wild-type counterpart group, which was also transfected with no virus, control virus vector, or AAV-p11. All virus transfections involved bilateral injection to the nucleus accumbens.

Figure 4:
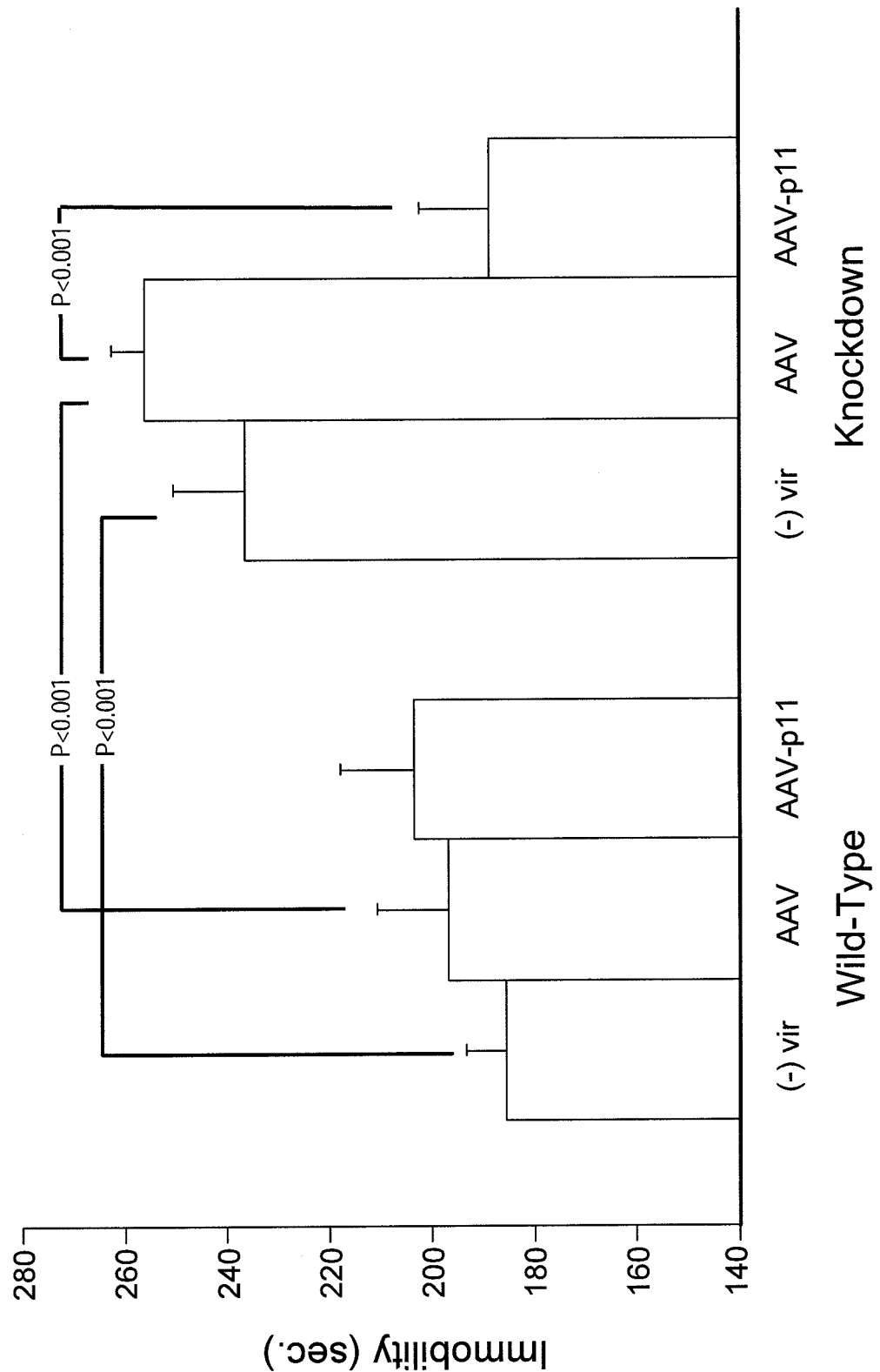
FIG. 4 is a graph comparing the results of tail suspension test (TST) in wild type (WT) and p11 knockdown mouse groups transfected with no virus ((−)vir), AAV control virus (AAV), and AAV virus encoding p11 (AAV-p11).
Figure 5:
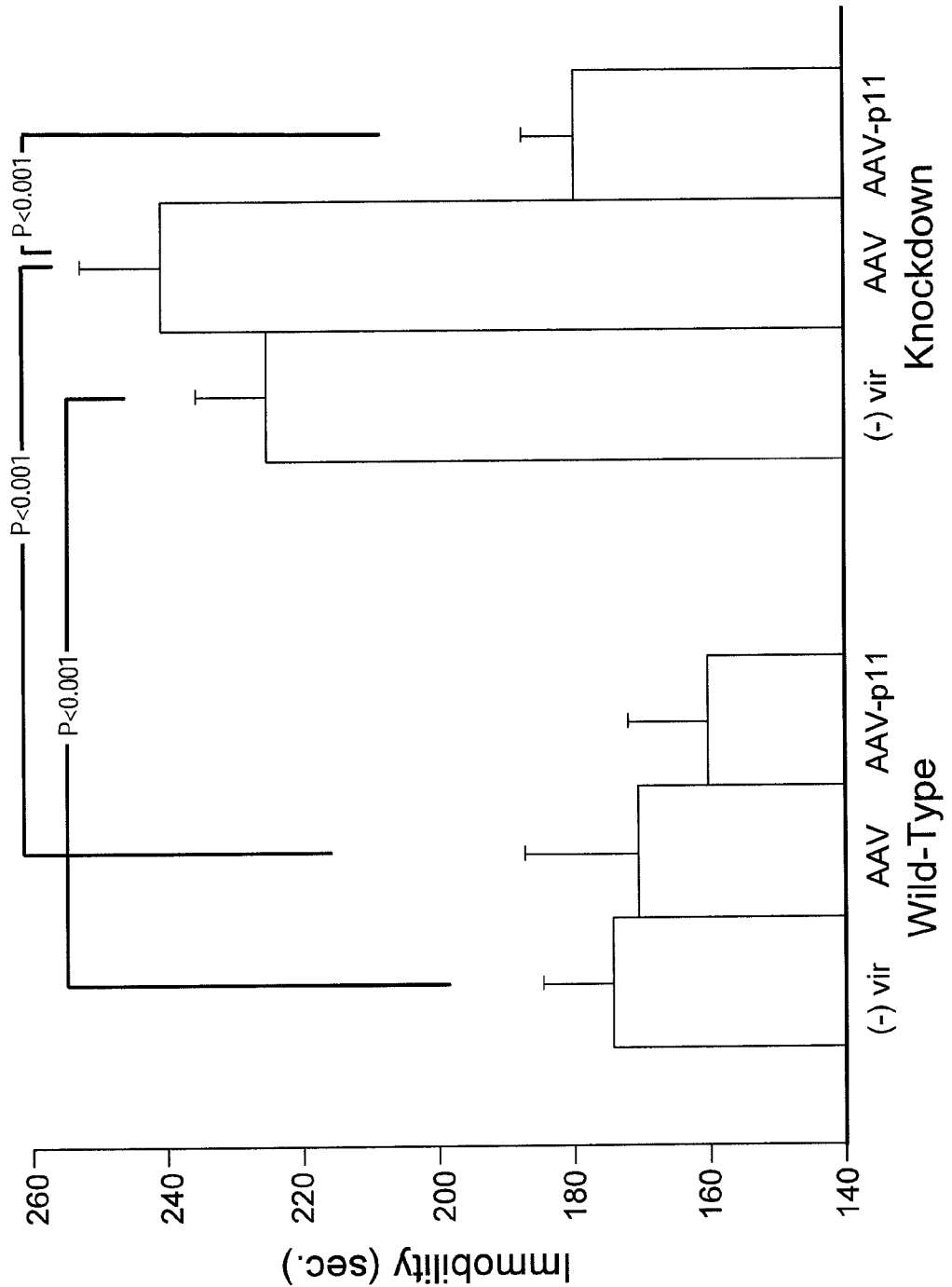
FIG. 5 is a graph comparing the results of forced swim test (FST) in wild type (WT) and p11 knockdown mouse groups transfected with no virus ((−)vir), AAV control virus (AAV), and AAV virus encoding p11 (AAV-p11).

The p11 knockdown mice transfected with control virus vector or no virus demonstrated increased immobility during TST and FST, relative to their counterpart wild type transfectants. See the test results set forth in FIGS. 4 and 5.

By contrast, the depressed phenotype of p11 knockdown mice was corrected by nucleus accumbens-targeted transfection of AAV-p11. When evaluated using TST and FST, knockdown mice transfected with AAV-p11 displayed durations of immobility similar to the wild type counterpart. This immobility was significantly less than p11 knockdown controls. See the test results set forth in FIGS. 4 and 5.

The foregoing results demonstrate that nucleus accumbens-targeted overexpression of p11 can correct a depressive phenotype by restoring a normal wild-type phenotype. These results differ from the previously reported non-targeted transgenic overexpression of p11, which produced an abnormal phenotype of general hyperactivity (Svenningson et al., supra, at 79). Unlike the previously reported transgenic overexpression of p11, the foregoing results indicate that gene therapy based on the transfection of a p11 nucleic can be used to treat depressive symptoms and restore a normal phenotype without inducing general hyperactivity.

Additionally, the foregoing results suggest that patients suffering from depression, e.g., major depressive disorder, may maintain low levels of p11 in the nucleus accumbens or in other areas of the brain. The results further indicate that p11 overexpression by gene therapy is useful as a clinical intervention for such depressive conditions.

EXAMPLE 5

This example demonstrates that the use of p11 to correct a depressive phenotype in mice is localized and cannot be recapitulated generically in all regions of the brain.

The anterior cingulated cortex of different mouse groups was injected with the AAV-p11siRNA construct or the control vector of Example 1. Knockdown of p11 in the anterior cingulated cortex had no significant effect and failed to reproduce the same depressive phenotype observed in mice with nucleus accumbens-targeted p11 knockdown.

The foregoing results are surprising inasmuch as the anterior cingulated cortex is a region that has been implicated in depression. Moreover, it was previously reported that p11 mRNA appeared to be decreased in preserved cryosections of anterior cingulated cortex from human patients that had been diagnosed with depression (Svenningson et al., supra, at FIG. 2(d), and page 79; see also supplementary online materials for Svenningson et al., supra, pages 4-5 and 15).

EXAMPLE 6

This example demonstrates p11 gene therapy in accordance with the invention. Generally, an AAV vector to increase expression of p11 (AAV-p11) is generated and selectively delivered as previously described in Kaplitt et al., *Lancet*, 369: 2097-105 (2007), which is specifically incorporated by reference herein in its entirety.

An AAV plasmid is engineered to include DNA encoding human p11 under the regulation of a cytomegalovirus enhancer-chicken β-actin promoter and woodchuck post-transcriptional regulatory element. Recombinant AAV-p11 vectors are packaged in human embryonic kidney (HEK) 293 cells and purified by heparin affinity chromatography, according to standard procedures and as previously described in Kaplitt et al., *Nat. Genet.*, 8: 148-154 (1994), and Luo et al., *Science*, 298: 425-429 (2002), both of which are specifically incorporated by reference herein in their entirety. The final formulation buffer is 1× phosphate-buffered saline solution. Genomic vector titres are measured by absolute quantification using ABI7000 Sequence Detection System (Applied Biosystems, Foster City, Calif., USA).

The AAV-p11 vector is diluted to $1 \times 10^{11}$ viral genomes (vg)/mL (low dose), $3 \times 10^{11}$ vg/mL (medium dose), and $1 \times 10^{12}$ vg/mL (high dose) with 1× phosphate-buffered saline solution. The bulk harvest and final formulated products are rigorously examined with lot-release testing, as per U.S. Federal Drug Administration (FDA) guidelines. Biosafety testing for mycoplasma, endotoxin, sterility, and adventitious viruses, and a general safety test, are performed (AppTec Laboratory Services, Philadelphia, Pa., USA).

Patients are divided into three groups that receive a low, medium, or high dose. All patients receive the same final injection volume of 50 μL pursuant to the following protocol. The nucleus accumbens is localized using Leksell stereotactic frame (Elekta Instrument AB, Stockholm, SE) and MRI image guidance. Intraoperative microelectrode recording is done with patients awake to verify the precise location of the nucleus accumbens. The tip of the microelectrode is then withdrawn to (what is judged to be) the center of the nucleus accumbens. 20 μL of 20% mannitol, followed by 45 μL of vector solution at the appropriate dose concentration (low, medium, or high), are drawn into a 100 μL Hamilton syringe. A 165-μm diameter vitreous silica infusion cannula is attached to the syringe, and the system is flushed until fluid is seen from the cannula tip. The syringe is inserted into a Harvard PicoPlus pump (Harvard, Holliston, Mass., USA), which is briefly run at 2 μL/min to assess flow. The tungsten microwire is withdrawn from the center of the bipolar microelectrode, and the infusion cannula is inserted, placing the tip at the same point in the center of the nucleus accumbens. Infusions are done for 100 min at 0.5 μL/min. After completion, the catheter is left in place for 5 minutes to reduce reflux. The catheter and outer tube are then withdrawn to place the catheter tip at the dorsal edge of the nucleus accumbens, which is left in place for a further 5 min. The guide tube and infusion catheter are then removed together to establish the integrity of the system, and the pump is run again to verify patency and flow after completion.

An ELISA assay is used to measure titres of anti-AAV antibodies in peripheral blood, and titres for neutralizing antibodies are also measured (see Kaplitt et al. (2007), supra). Anti p11 antibodies from patient serum samples are quantified with an ELISA and compared with serum samples from healthy blood-donor serum samples.

EXAMPLE 7

This example supports the therapeutic relevance of p11 in treating psychiatric disorders, especially depression, in humans.

The level of p11 protein in the nucleus accumbens in the post-mortem brains of depressed and control humans patients was analyzed by quantitative western blot with an anti-p11 monoclonal antibody. Each of the control group of normal, i.e., non-depressed, patients, and the group of depressed patients contained 17 patients. Moreover, the control group of normal patients was age and sex matched to the depressed patient group. The determined p11 protein levels were normalized to actin.

The p11/actin level in the nucleus accumbens of the control group was determined to be approximately 0.73+/−0.1, while the p11/actin level in the nucleus accumbens of the depressed patient group was determined to be approximately 0.94+/− 0.1, i.e., about 20-30% higher.

The foregoing results evidence the importance of p11 in psychiatric disorders, especially depression, and support the therapeutic relevance of p11 in the treatment of psychiatric disorders in humans.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a mammal having major depressive disorder or refractory depression, which method comprises directly delivering to the nucleus accumbens of the mammal an adeno-associated virus vector comprising a p11 nucleic acid sequence that encodes a human p11 protein wherein the p11 nucleic acid sequence is operably linked to an expression control sequence, whereby the major depressive disorder or the refractory depression in the mammal is treated.

2. The method of claim 1, wherein the mammal has major depressive disorder.

3. The method of claim 1, wherein the mammal has refractory depression.

4. The method of claim 1, wherein the p11 nucleic acid sequence comprises SEQ ID NO: 1.

5. The method of claim 1, wherein the human p11 protein comprises the amino acid sequence of SEQ ID NO: 2.

6. A method of improving the responsiveness of a mammal having major depressive disorder or refractory depression to treatment for the major depressive disorder or the refractory depression, which method comprises:

(a) directly delivering to the nucleus accumbens of the mammal an adeno-associated virus vector comprising a p11 nucleic acid sequence that encodes a human p11 protein whereby the p11 nucleic acid sequence is operably linked to an expression control sequence, and (b) subjecting the mammal to treatment for major depressive disorder or refractory depression other than with gene therapy, whereby the mammal's responsiveness to treatment for the major depressive disorder or the refractory depression is improved.

7. The method of claim 6, wherein the mammal has major depressive disorder.

8. The method of claim 6, wherein the mammal has refractory depression.

9. The method of claim 6, wherein the treatment comprises a pharmacological treatment.

10. The method of claim 9, wherein the pharmacological treatment comprises administration of a pharmaceutical agent selected from the group consisting of amitriptyline, clomipramine, desipramine, doxepin, imipramine, nortriptyline, protriptyline, fluoxetine, fluvoxamine, paroxetine, sertaline, citalopram, escitalopram oxalate, duloxetine, venlafaxine, mirtazapine, nefazodone, desyrel, and combinations thereof.

11. The method of claim 6, wherein the treatment comprises electroconvulsive therapy (ECT).

12. The method of claim 6, wherein the p11 nucleic acid sequence comprises SEQ ID NO: 1.

13. The method of claim 6, wherein the human p11 protein comprises the amino acid sequence of SEQ ID NO: 2.

* * * * *

SEQUENCE LISTING

```
<160> NUMBER OF SEQ ID NOS: 4

<210> SEQ ID NO 1
<211> LENGTH: 291
<212> TYPE: DNA
<213> ORGANISM: Homo sapiens
<220> FEATURE:
<221> NAME/KEY: CDS
<222> LOCATION: (1)..(291)
```

```
<400> SEQUENCE: 1 atg cca tct caa atg gaa cac gcc atg gaa acc atg atg ttt aca ttt      48
Met Pro Ser Gln Met Glu His Ala Met Glu Thr Met Met Phe Thr Phe
1               5                   10                  15 cac aaa ttc gct ggg gat aaa ggc tac tta aca aag gag gac ctg aga      96
His Lys Phe Ala Gly Asp Lys Gly Tyr Leu Thr Lys Glu Asp Leu Arg
                20                  25                  30 gta ctc atg gaa aag gag ttc cct gga ttt ttg gaa aat caa aaa gac     144
Val Leu Met Glu Lys Glu Phe Pro Gly Phe Leu Glu Asn Gln Lys Asp
            35                  40                  45 cct ctg gct gtg gac aaa ata atg aag gac ccg gac cag tgt aga gat     192
Pro Leu Ala Val Asp Lys Ile Met Lys Asp Pro Asp Gln Cys Arg Asp
        50                  55                  60 ggc aaa gtg ggc ttc cag agc ttc ttt tcc cta att gcg ggc ctc acc     240
Gly Lys Val Gly Phe Gln Ser Phe Phe Ser Leu Ile Ala Gly Leu Thr
65                  70                  75                  80 att gca tgc aat gac tat ttt gta gta cac atg aag cag aag gga aag     288
Ile Ala Cys Asn Asp Tyr Phe Val Val His Met Lys Gln Lys Gly Lys
                85                  90                  95 aag                                                                  291
Lys

<210> SEQ ID NO 2
<211> LENGTH: 97
<212> TYPE: PRT
<213> ORGANISM: Homo sapiens

<400> SEQUENCE: 2

Met Pro Ser Gln Met Glu His Ala Met Glu Thr Met Met Phe Thr Phe
1               5                   10                  15

His Lys Phe Ala Gly Asp Lys Gly Tyr Leu Thr Lys Glu Asp Leu Arg
                20                  25                  30

Val Leu Met Glu Lys Glu Phe Pro Gly Phe Leu Glu Asn Gln Lys Asp
            35                  40                  45

Pro Leu Ala Val Asp Lys Ile Met Lys Asp Pro Asp Gln Cys Arg Asp
        50                  55                  60

Gly Lys Val Gly Phe Gln Ser Phe Phe Ser Leu Ile Ala Gly Leu Thr
65                  70                  75                  80

Ile Ala Cys Asn Asp Tyr Phe Val Val His Met Lys Gln Lys Gly Lys
                85                  90                  95

Lys

<210> SEQ ID NO 3
<211> LENGTH: 649
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (112)..(402)

<400> SEQUENCE: 3
agaatacact cacaagccac tccgctgctc gcctctccgc cccgcgtcca gctcgcccag     60
ctcgcccagc gtccgccgcg cctcgccaag gcttcaacgg accacaccaa a atg cca    117
                                                         Met Pro
                                                         1 tct caa atg gaa cac gcc atg gaa acc atg atg ttt aca ttt cac aaa     165
Ser Gln Met Glu His Ala Met Glu Thr Met Met Phe Thr Phe His Lys
        5                   10                  15
```

```
ttc gct ggg gat aaa ggc tac tta aca aag gag gac ctg aga gta ctc      213
Phe Ala Gly Asp Lys Gly Tyr Leu Thr Lys Glu Asp Leu Arg Val Leu
    20                  25                  30 atg gaa aag gag ttc cct gga ttt ttg gaa aat caa aaa gac cct ctg      261
Met Glu Lys Glu Phe Pro Gly Phe Leu Glu Asn Gln Lys Asp Pro Leu
35                  40                  45                  50 gct gtg gac aaa ata atg aag gac ctg gac cag tgt aga gat ggc aaa      309
Ala Val Asp Lys Ile Met Lys Asp Leu Asp Gln Cys Arg Asp Gly Lys
                55                  60                  65 gtg ggc ttc cag agc ttc ttt tcc cta att gcg ggc ctc acc att gca      357
Val Gly Phe Gln Ser Phe Phe Ser Leu Ile Ala Gly Leu Thr Ile Ala
                70                  75                  80 tgc aat gac tat ttt gta gta cac atg aag cag aag gga aag aag          402
Cys Asn Asp Tyr Phe Val Val His Met Lys Gln Lys Gly Lys Lys
            85                  90                  95 taggcagaaa tgagcagttc gctcctccct gataagagtt gtccaaaggg tcgcttaagg    462
aatctgcccc acagcttccc ccatagaagg atttcatgag cagatcagga cacttagcaa    522
atgtaaaaat aaaatctaac tctcatttga caagcagaga aagaaaagtt aaataccaga    582
taagcttttg attttgtat tgtttgcatc cccttgccct caataaataa agttcttttt     642
tagttcc                                                              649

<210> SEQ ID NO 4
<211> LENGTH: 19
<212> TYPE: DNA
<213> ORGANISM: Artificial Sequence
<220> FEATURE:
<223> OTHER INFORMATION: Small interfering RNA (siRNA)

<400> SEQUENCE: 4
gtgggcttcc agagcttct                                                 19
```